United States Patent [19]

Bar et al.

[11] Patent Number: 5,202,338
[45] Date of Patent: Apr. 13, 1993

[54] DIHYDROQUINOLINE DERIVATIVES, PHARMACEUTICAL COMPOSITIONS AND METHODS OF USE OF DIHYDROQUINOLINE DERIVATIVES AS MODULATORS OF THE ARACHIDONIC ACID CASCADE

[76] Inventors: Vilmos Bar; Zsuzsa Pollak, both of Otthon u. 27, H-1118 Budapest; Istvan Penzes, Josef A. u. 24, H-2092 Budakeszi, all of Hungary

[21] Appl. No.: 606,424

[22] Filed: Oct. 31, 1990

[51] Int. Cl.$^5$ .................. C07D 401/06; A61K 31/47
[52] U.S. Cl. .................................. 514/314; 546/176; 546/172; 546/169
[58] Field of Search ................... 546/167, 172, 169; 514/314

[56] References Cited

U.S. PATENT DOCUMENTS

| | | | |
|---|---|---|---|
| 4,025,631 | 5/1977 | Bar et al. | 424/258 |
| 4,046,765 | 9/1977 | Bar et al. | 260/288 |
| 4,356,305 | 10/1982 | Szantay et al. | 546/51 |
| 4,363,910 | 12/1982 | Ambrus et al. | 546/172 |
| 4,490,394 | 12/1984 | Ambrus et al. | 426/2 |
| 4,568,696 | 2/1986 | Smerbeck et al. | 514/688 |
| 4,708,964 | 11/1987 | Allen | 514/533 |
| 4,761,424 | 8/1988 | Carethers et al. | 514/443 |
| 4,868,195 | 9/1989 | Carethers et al. | 514/375 |
| 4,868,199 | 9/1989 | Carethers et al. | 514/411 |
| 4,868,200 | 9/1989 | Carethers et al. | 514/418 |
| 4,868,205 | 9/1989 | Carethers et al. | 514/456 |
| 4,921,871 | 5/1990 | Carethers et al. | 514/432 |

FOREIGN PATENT DOCUMENTS

| | | |
|---|---|---|
| 3025656 | 1/1981 | Fed. Rep. of Germany . |
| 162358 | 9/1971 | Hungary . |
| 1390991 | 4/1975 | United Kingdom . |

OTHER PUBLICATIONS

Zs. Pollak et al. The European Repiratory Journal, vol. 1, Supplement 2, 1988.
Zs. Pollak et al. 6th Congress of the European Society of Pneumology, Amsterdam, Free University, p. 180 (1987).
D. J. Baumann et al., "Flavonoids and Related Compounds as Inhibitors of Arachidonic Acid Peroxidase", Prostaglandins, vol. 20, No. 4, pp. 627-637 (Oct. 1980).
Zs. Pollak et al., Strahlentherapie, 154, pp. 499 to 502 (1978).
Zs. Pollak et al., Acta Radiol. Scand., 18, pp. 97 to 101 (1979).
Erdelyi et al., Strahlenterapie, 156, pp. 198 to 200 (1980).
G. Kovacs, Strahlentherapie, 160, pp. 590 to 593 (1984).
Borzsonyi et al., Toxicol. Letters, 7, pp. 285-288 (1981).
J. Feher et al., Acta Physiol. Hung., 64, pp. 401 to 407 (1984).
S. Sulyok et al., Acta Physiol. Hung., 64, pp. 437 to 444 (1984).
Chemical Abstracts. Aliphatics, vol. 92, pp. 41264 (1980).
Javor et al., Int. J. Tiss. React. 1, pp. 35 to 40 (1986).
Bengt Samuelsson, "The Leukotrienes, Highly Biologically Active Substances Involved in Allergy and Inflammtion" Angew. Chem. Int. Ed. Engl. 21:902-910 (1982).
J. Feher and A. Vereckei, "Importance of Free Radical Reactions in the Medicine," Ed. Biogal Pharmaceutical Works, p. 98 (1985).
Tetason, J. E. et al., Brit. J. Pharmacol., 1988 94: 528-529.
Salmon, J. A. Prostaglandins, 1978 15: 383-397.
Salmon, J. A. et al., Prostaglandins, 1982, 24:225-235.
Zs. Pollak, dissertation, "Development of a Radio-sensitizing Antioxidant and Use Thereof in the Oncoradiologic Practice" (Library of Hungarian Academy of Sciences, 1979.

Primary Examiner—David B. Springer
Attorney, Agent, or Firm—Woodcock Washburn Kurtz Mackiewicz & Norris

[57] ABSTRACT

The present invention relates to novel dihydroquinoline derivatives, pharmaceutical compositions and methods of use of dihydroquinoline derivatives as modulators of the arachidonic acid cascade. The novel dihydroquinoline derivatives of this invention are useful for the treatment of diseases, such as asthma, where products of the arachidonic acid cascade contribute to the disease.

19 Claims, No Drawings

DIHYDROQUINOLINE DERIVATIVES, PHARMACEUTICAL COMPOSITIONS AND METHODS OF USE OF DIHYDROQUINOLINE DERIVATIVES AS MODULATORS OF THE ARACHIDONIC ACID CASCADE

FIELD OF THE INVENTION

The present invention relates to novel dihydroquinoline derivatives, pharmaceutical compositions and methods of use of dihydroquinoline derivatives as modulators of the arachidonic acid cascade. The dihydroquinoline derivatives of this invention are useful for the treatment of diseases, such as asthma, where products of the metabolism of arachidonic acid contribute to the disease.

BACKGROUND OF THE INVENTION

Arachidonic acid serves as the biological precursor for a family of physiologically active eicosanoids. These eicosanoids include products derived from the metabolism of arachidonic acid, the two major routes of which are the lipoxygenase pathway and the cyclooxygenase pathway.

Lipoxygenase pathway products such as leukotrienes (LT), function as regulators of allergic and inflammatory reactions. Dorland's Illustrated Medical Dictionary, 27th Ed., W. B. Saunders Co., Phila., Pa., (1988) Leukotrienes are identified by letters with subscripts indicating the number of double bonds in the molecule. Id. Some leukotranes, e.g., $LtB_4$, stimulate the movement of leukocytes, while others, e.g., $LTC_4$, $LTD_4$, and $LTE_4$, constitute slow reacting substance of anaphylaxis (SRS-A), which causes bronchial constriction and other allergic reactions. Id. The role of leukotrienes according to J. Feher, G. Csomos and A. Vereckei ("Free Radical Reactions in Medicine", Springer Verlag, Berlin, Heidelberg, New York, Tokyo, 1987, p. 29) is important in the regulation of neutrophil and eosinophil function, chemotaxis, chemokinesis, stimulation of guanylate cyclase, modest release of lysosomal enzymes, humoral activities, contraction of smooth muscle, alteration in the permeability of microvasculature, constriction of peripheral pulmonary airways and trachea.

The cyclooxygenase pathway leads to the cyclic endoperoxides (PGG and PGH) and subsequent metabolic products. The inhibition of their biosynthesis is now widely recognized as a mechanism of the nonsteroidal anti-inflammatory drugs such as aspirin. Goodman and Gillman's "The Pharmacological Basis of Therapeutics," MacMillan Publishing Co., New York, N.Y. 7th Ed., Ch. 28, (1985). One of the limitations of the aspirin-like drugs is their inability to inhibit the metabolism of arachidonic acid by lipoxygenases. Id at 663. It is believed that inhibition of cyclooxygenase can lead to increased formation of leukotrienes, which may play a role in the production of symptoms of hypersensitivity in some individuals following the administration of aspirin and aspirin-like drugs. Id.

U.S Pat. No. 4,708,964 discloses compounds unrelated to dihydroquinoline useful for the inhibition of lipoxygenase in humans. As inhibitors of lipoxygenase, these compounds are disclosed to be useful in the treatment of psoriasis, cell proliferation, skin allergies, insect bites, allergic rhinitis, conjunctivitis, hay fever, bronchial asthma, allergic gastroenteritis, uterine contractions, hyperactivity of the colon and bronchospasms.

It is known from the publication of D. J. Baumanor et al., "Flavonoids and Related Compounds as Inhibitors of Arachidonic Acid Peroxidase", Prostaglandins, Vol. 20, No. 4, pp 627–637 (Oct 1980) that many flavonoids, incl. Catergan (The Merck Index, Eleventh Edition, 1988), are lipoxygenase and cylooxgenase pathway inhibitors. However, their use is associated frequency with hemolytic anemia of fatal outcome, so e.g. Catergan was neither withdrawn from the clinical practice or its application had been strongly limited in several European countries, including Hungary.

Carethers et al. in a series of patents, of which U.S. Pat. No. 4,921,871 is illustrative, disclose enolamides which inhibit lipoxygenase or the biosynthesis or biochemical action of leukotrienes and, therefore, are taught as useful in the treatment or amelioration of a number of diseases whose pathogenesis involves the production of the leukotrienes and other lipoxygenase-derived products. These lipoxygenase inhibitors aid in the prevention of tissue damage and inflammation which result from infiltration of leukocytes, release of tissue digesting lysosomal enzymes, and changes in the permeability and contractile state of smooth muscle tissue. Carethers et al. further discloses specific conditions in which such lipoxygenase-inhibiting or leukotriene-antagonizing compounds and pharmaceutical compositions are useful and these include allergy, asthma, arthritis, skin disorders including psoriasis and acne, inflammation, inflammatory bowel diseases, pain, and cardiovascular disorders including myocardial ischemia and infarction, angina, arrhythmias, stroke, and atherosclerosis.

U.S. Pat. No. 4,568,696 discloses combinations of non-steroidal anti-inflammatory compounds useful in the treatment of pain, inflammation, swelling and other related symptoms. Such combinations are inhibitors of both the lipoxygenase and cyclooxygenase pathways, and it is theorized, that this inhibition of both pathways, is the mechanism by which the compounds of this disclosure reduce and control pain and inflammation.

It is known from the Hungarian patent specification No. 162,358 or the equivalent British patent specification No. 1,390,991 or the equivalent German patent specification No. 2,265,400 that 2,2,4-trimethyl-1,2-dihydroquinoline and its substituted derivatives, except the derivatives substituted on the nitrogen and the carbon in position 6 (hereinafter named "acetoanils"), are capable of reacting with aliphatic $C_{1-4}$ aldehydes in a condensation reaction. It has also been mentioned in these patent specifications that the dihydroquinoline derivatives thus prepared are highly effective antioxidants or radical scavengers with a very low toxicity. Out of the compounds described in those patent specifications 6,6'-methylene-bis(2,2,4-trimethyl-1,2-dihydroquinoline) (hereinafter referred to as "MTDQ") has been used in the clinical practice as a radio sensitizing agent in the ionization radiotherapy of malignant tumors. In this connection, the following literature references and patent specifications can be cited: U.S. Pat. Nos. 4,025,631 and 4,046,765; Zs. Pollak et al., Strahlentherapie, 154, pages 499 to 502 (1978), a paper publishing a presumable mechanism of action, too in addition to the clinical results; Zs. Pollak et al., Acta Radiol. Scand., 18, pages 97 to 101 (1979); Erdelyi et al., Strahlentherapie, 156, pages 198 to 200 (1980); G. Kovacs, Strahlentherapie, 160, pages 590 to 593 (1984); and A. U.

Schratter, *Wiener Klinische Wochenschrift*, 15, pages 518 to 522 described in the latter article.

Alkaline metal salts of 6,6'-methylene-bis(2,2-dimethyl-1,2-dihydroquinoline-4-methane sulfonate) derivatives have been described in our published German patent application Ser. No. 3,025,656 or equivalent U.S. Pat. No. 4,356,306 as water-soluble derivatives (hereinafter named "MTDQ-DA"). Borzsonyi et. al., *Toxicol. Letters*, 7, pages 281 to 285 (1981) stated that MTDQ is liberated in vivo from these compounds showing a protective effect against carcinogens J. Feher et al., *Acta Physiol. Hung.*, 64, pages 401 to 407 (1984) described the hepatoprotective action of these compounds whereas S. Sulyok et al., *Acta Physiol. Hung.*, 64, pages 437 to 44 (1984) reported on an antiatherosclerotic effect.

As a comprehensive work, the dissertation of candidate's degree of Zs. Pollak entitled "Development of a Radiosensitizing Antioxidant and Use Thereof in the Oncoradiologic Practice" (in Hungarian; Library of the Hungarian Academy of Sciences, 1979) can be cited. The following citation is found on page 30 of this dissertation, in the chapter entitled "The Biochemical Conception of the Synthesis of MTDQ": "In the course of our synthetic work it was aimed to maintain the effectivity of the antioxidant and simultaneously, to decrease its toxicity. This was achieved by increasing the molecular weight on the one hand and by taking care, on the other hand, that the ratio of the molecular weight to the number of functional groups would not be higher".

Aliphatic ketones can also be used instead of aliphatic aldehydes in the preparation of compounds of this kind as the following citation is found in Gy. Bruckner's textbook entitled "Organic Chemistry" (Ed. Tankonyvkiado, Budapest, 1954; in Hungarian) Vol. I., page 396: "Ketones show condensation reactions analogous to those of aldehydes".

Recently Javor et al., *Int. J. Tiss. React.* 1, pages 35 to 40 (1986) reported on the protective action of compounds of the above type on the gastrointestinal mucosa. Zs. Pollak et al., described their utility for the protection from damages induced by free radicals in the acute respiratory insufficiency. MTA Symposion, January 7 and 8, 1986, Szeged, Abstracts of Proceedings, page 27; 6th Congr. Eur. Soc. Pneumonol, Amsterdam from Aug. 31 to Sep. 5, 1987, Subm. Abstr. No. 447,180 and Abstr. No. 275,276 of the 7th Congr. Eur. Pulm. Budapest, from Sep. 4 to 9, 1988.

It should be emphasized that the therapeutic effects listed above are based on the effect exerted on the cyclooxygenase system and within this, on the shift of the prostacyclin/thromboxane balance in favor of prostacyclin. G. Deby-Dupont et al., *Intensive Care Med.*, 13. pages 167 to 174 (1987) refer thereto that, among the therapeutic effects discussed above, the action protecting from the acute respiratory insufficiency is based on this mechanism of action.

It has now been found, that the dihydroquinoline derivatives of this invention, modulate pathways in the metabolism of arachidonic acid. Arachidonic acid pathways include, but are not limited to, cyclooxygenase and lipoxygenase. Thus, the compounds of this invention are useful in the treatment of a wide variety of pathological conditions where products of the pathways of the metabolism of arachidonic acid, i.e. the cyclooxygenase and the lipoxygenase pathways, contribute to the pathogenesis. At the same time, while decreasing the concentration of leukotrienes, they increase the ratio of prostacycline/thromboxane $A_2$. Moreover, the compounds of this invention unexpectedly normalize the pathologically changed cytochrome C and P 450 values, said latter two compounds being known as the initiators of the toxic generation of oxygen free radicals from molecular oxygen.

SUMMARY OF THE INVENTION

There is provided by this invention a compound of the formula:

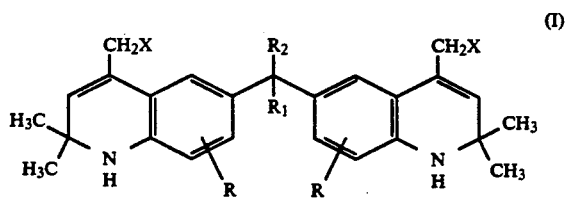

wherein:

$R_1$ is a $C_{1-6}$ alkyl group, a $(C_{1-6})$ alkylcarbonyl group, a $C_{2-6}$ alkenyl group, a hydroxy group, a $C_{1-6}$ alkoxy group, a $C_{2-6}$ alkenyloxy group, a halo-$(C_{1-6})$ alkyl group, a halo-$(C_{2-6}$ alkenyl group, a hydroxy -$(C_{1-6})$ alkyl group, a $(C_{1-6})$ alkoxy-$(C_{1-6})$ alkyl group, a $(C_{2-6})$-alkenyloxy-$(C_{1-6})$ alkyl group, a halo-$(C_{1-6})$ alkoxy-$(C_{1-6})$ alkyl group, a halo-$(C_{2-6})$ alkenyloxy-$(C_{1-6})$ alkyl group, a carboxy-$(C_{1-6})$ alkyl group, a $(C_{1-6})$ alkoxycarbonyl-$(C_{1-6})$ alkyl group, a $(C_{2-6})$ alkenyloxycarbonyl-$(C_{1-6})$-alkyl group, a halo-$(C_{2-6})$ alkoxycarbonyl-$(C_{1-6})$-alkyl group, a halo-$(C_{2-6})$ alkenyloxycarbonyl-$(C_{1-6})$ alkyl group, a $(C_{2-6})$ alkenylcarbonyl group, a $(C_{2-6})$ alkanoyl-$(C_{1-6})$ alkyl group, a $C(=0)$ H—$C_{1-6}$ alkyl group, a nitro-$(C_{1-6})$ alkyl group or a nitroso-$(C_{1-6})$ alkyl group or a group of the formula —$NR_3R_4$ and in the latter $R_3$ and $R_4$ may represent, independently from each other, a hydrogen atom, a $C_{1-6}$ alkyl group, a $C_{2-6}$ alkenyl group, a halo-$C_{1-6}$ alkyl group or a halo-$C_{2-6}$ alkeynl group;

R is the hydrogen or its meaning is identical to the meaning of $R_1$;

$R_2$ is hydrogen or its meaning is identical to the meaning of $R_1$;

with the proviso that $R_2$ means an alkyl group when $R_1$ is also an alkyl group and with the further proviso that it cannot be hydroxy; and X is hydrogen or —$SO_2Me$ group, where Me is an alkaline metal or earth alkaline metal atom, with the proviso that Me cannot mean barium; and if $R_1$ is an alkyl group and $R_2$ is hydrogen, then R is other than hydrogen or methyl;

as well as their pharmaceutically acceptable acid addition salts.

Also provided by the invention is a pharmaceutical composition comprising the compound of formula I in a pharmaceutically acceptable carrier.

Further provided by this invention is a method of substantially simultaneously inhibiting a cyclooxygenase pathway and a lipoxygenase pathway in a mammal suspected of requiring said inhibition comprising administering to the mammal an effective amount of the compound of formula (I) or an effective amount of a compound of the formula:

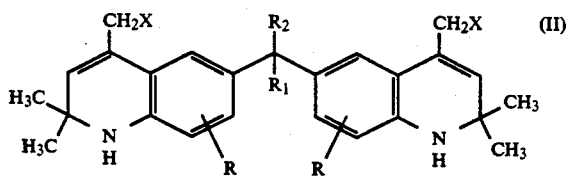

wherein:

$R_1$ is a $C_{1-6}$ alkyl group, a $(C_{1-6})$ alkylcarbonyl group, a $C_{2-6}$ alkenyl group, a hydroxy group, a $C_{1-6}$ alkoxy group, a $C_{2-6}$ alkenyloxy group, a halo-$(C_{1-6})$ alkyl group, a halo-$(C_{2-6})$ alkenyl group, a hydroxy-$(C_{1-6})$alkyl group, a $(C_{1-6})$ alkoxy-$(C_{1-6})$ alkyl group, a $(C_{2-6})$-alkenyloxy-$(C_{1-6})$alkyl group, a halo-$(C_{1-6})$alkoxy-$(C_{1-6})$alkyl group, a halo-$(C_{2-6})$alkenyloxy-$(C_{1-6})$ alkyl group, a carboxyl-$(C_{1-6})$alkyl group, a $(C_{1-6})$ alkoxycarbonyl-$(C_{1-6})$ alkyl group, a $(C_{2-6})$ alkenyloxycarbonyl-$(C_{1-6})$alkyl group, a halo-$(C_{1-6})$ alkoxycarbonyl-$(C_{1-6})$-alkyl group, a halo-$(C_{2-6})$ alkenyloxycarbonyl-$(C_{1-6})$alkyl group, a $(C_{2-6})$ alkenylcarbonyl group, a $(C_{2-6})$alkanoyl-$(C_{1-6})$ alkyl group, a $C(=O)H-C_{1-6}$ alkyl group, a nitro-$(C_{1-6})$ alkyl group or a nitroso-$(C_{1-6})$ alkyl group or a group of the formula $-NR_3R_4$ and in the latter $R_3$ and $R_4$ may represent, independently from each other, a hydrogen atom, a $C_{1-6}$ alkyl group, a $C_{2-6}$ alkenyl group, a halo-$C_{1-6}$ alkyl group or a halo-$C_{2-6}$ alkenyl group;

R is hydrogen or its meaning is identical to the meaning of $R_1$, $R_2$ is hydrogen or its meaning is identical to the meaning of $R_1$, with the proviso that it cannot be hydroxy; and X is hydrogen or $-SO_2Me$ group, where Me is an alkaline metal or earth alkaline metal atom, with the proviso that Me cannot mean barium;

as well as their pharmaceutically acceptable acid addition salts.

Additionally provided by the invention is a method of treating a pathological condition where products of the metabolism of arachidonic acid contribute to the condition comprising administering to a mammal in need of such treatment an effective amount of the compound of formula I or an effective amount of the compound of formula II.

Additionally provided by this invention is a method of normalizing pathologically changed cytochrome C and P450 values comprising administering to a mammal in need of such treatment an effective amount of the compound of formula I or an effective amount of the compound of formula II.

DETAILED DESCRIPTION OF THE INVENTION

It has surprisingly been recognized that the 1,2-dihydroquinoline derivatives of formula I and II and their pharmaceutically acceptable acid addition salts (which can always be prepared, except when X is an $SO_3Me$ group) exert an effect not only on the cyclooxygenase pathway, as reported in the literature cited herein, but substantially simultaneously on the lipoxygenase pathway. Thus, they can be utilized in the treatment of diseases wherein, according to the current literature, the use of compounds acting on the cyclooxygenase system is contraindicated. However, the compounds of this invention inhibit only the pathologically acting thromboxane $A_2$, not, however, the prostacycline of vital importance. Here, J. Feher and A. Vereckei can be cited "Importance of Free Radical Reactions in the Medicine," Ed. Biogal Pharmaceutical Works, page 98 (1985)] who suggest thereto that, on shifting the balance towards the lipoxygenase reactions by inhibition of the cyclooxygenase reactions, SRS-A, a compound inducing asthma, is formed.

The alkyl groups or moieties in the meaning of $R_1$, $R_2$, R, $R_3$ and $R_4$ may be straight or branched chained alkyl groups comprising 1 to 6 carbon atoms, e.g. a methyl, ethyl, propyl, isopropyl, n-butyl, sec-butyl, pentyl, isopentyl or hexyl group. The alkenyl groups or moieties may be straight or branched chain alkenyl groups comprising 2 to 6 carbon atoms, e.g. an allyl or propenyl group. The alkoxy groups or moieties may be straight or branched chained groups deriving from the above listed alkyl groups, e.g. methoxy, ethoxy, propoxy, isopropoxy, n-butoxy, sec-butoxy, pentoxy or hexyloxy group. The alkanoyl group may be a straight or branched chained group comprising 2 to 6 carbon atoms, e.g. acetyl or propionyl group. Under "halo" preferably chloro, bromo or iodo is understood. The halogenated groups may carry one or more halo atom(s) as substituents.

In pharmaceutical compositions according to the invention, the amount of the active ingredients of formula I and II can suitably be varied between 10 and 90% by weight, depending on the dosage form actually used. The pharmaceutical compositions according to the invention can be formulated as liquid or solid preparations well known from the pharmaceutical practice such as tablets, capsules, powders, ampouled compositions and the like.

Concerning the preparation of the compounds of formula II, U.S. Pat. Nos. 4,025,631 and 4,046,765, which patents are incorporated by reference, can be referred to.

The new compounds of formula I can be prepared by using the methods described in U.S. Pat. Nos. 4,025,631 and 4,046,765 except that, ketonaldehydes, unsaturated aldehydes, aliphatic ketones or their derivatives are utilized instead of the aliphatic aldehydes as reactants with 2,2,4-trimethyl-1,2-dihydroquinoline. The derivatives bearing a sulfonic acid group can be prepared in a known way by using the process described in U.S. Pat. No. 4,365,306 which patent is incorporated by reference. It should be noted that in the course of preparing water-soluble sulfonic acid derivatives, it is suitable to heat the sulfonating reaction mixture with concentrated sulfuric acid at about 60 to about 90° C. until a sample of the mixture becomes completely water-soluble. Thereafter, the reaction mixture is suitably worked up in such a way that it is poured into a sodium or potassium chloride solution to precipitate the alkaline metal salt of the disulfonic acid. A product with a higher purity can be obtained by portionwise adding an earth alkaline metal hydroxide to the reaction mixture after the reaction. In this case, the salt of the disulfonic acid formed is maintained in solution whereas the corresponding sulfate salt is precipitated. Subsequently, the earth alkaline metal salt is converted to a potassium or sodium salt by reacting it with an equimolar amount of potassium or sodium carbonate.

Alternatively, the working-up can suitably be carried out in such a way that after sulfonation, the reaction mixture is poured into about 2.5 to about 9 volumes of water or an organic solvent, preferably toluene, ethyl acetate or acetone or their mixture. Then the free sulfonic acid can be recrystallized from water and converted to an alkaline metal salt.

The compounds of this invention can be administered by any means that effects modulation of an arachidonic acid pathway in mammals. For example, administration can be oral and/or parenteral, e.g., subcutaneous, intravenous, intraperitoneal, or topical. The dosage administration will be dependent upon the age, health and weight of the recipient and the kind of concurrent treatment, if any, and frequency of treatment.

Daily dosage of active ingredient compounds can be determined by one skilled in the art, and generally will be from about 1.0 mg to about 100 mg per kg of body weight when non-locally applied. Preferably, the daily dose is in the range from 10 to 25 mg/kg of body weight. The compounds can be employed in dosage forms such as tablets, capsules, powder packets or liquid solutions, or elixirs for oral administration; or for parenteral administration, sterile liquid solutions or suspensions. For topical use, the compounds may be prepared in aerosol sprays, creams, gels and ointments such as vanishing creams and ointments having a polyethylene glycol base; and in other such carriers known to the art.

An example of an advantage of using the pharmaceutical compositions according to the invention, is that steroidal hormone-dependent patients can be treated without employing steroidal hormones or reduced dosage of steroids. It is commonly know that steroidal hormones, e.g. prednisolone, exhibit harmful side effects such as decrease in the resistance to infections, elevated blood pressure; steroid diabetes; renal injuries; exhaustion of the adrenal cortex; and ulceration of the gastrointestinal mucosa frequently accompanied by bleedings. Other severe side effects are discussed in detail in a book entitled "Guide to the Prescription of Pharmaceutical Compositions," *Ed. Medicina Budapest*, pages 562 to 564 (1988). Steroidal hormones inhibit the formation of arachidonic acid and therefore, they suppress not only the formation of the harmful thromboxane but also that of prostacyclin which is of vital importance.

It should be noted for the sake of completeness that, in the course of practical use of the compositions according to the invention, the medical practitioner may employ other drugs in combination with a composition according to the invention for the treatment of diseases, such as the use of allopurinol in combination with a compound of formula I or II in the treatment of asthma.

The compounds of this invention as inhibitors of cyclooxygenase and lipoxygenase pathways, have utility in the treatment of a variety of pathological conditions where products of the metabolism of arachidonic acid contribute to the pathogenesis. Such conditions include for example: allergy; asthma; arthritis; skin disorders, e.g., burns, psoriasis, acne and insect bites; inflammation; conjunctivitis; inflammatory bowel disease; pain; cardiovascular disorders, e.g., myocardial infarction, angina, stroke; tumor suppression; obstructive airway and lung disease: pancreatitis; osteoporosis; and cataracts senilis; Alzheimer's disease; cerebrovascular syndrome; injuries of the central nervous system; Parkinson's disease; ischemic cerebrovascular disease; necrotic colitis; hypersensitivity reactions, syndromes and symptoms; prevention and treatment of ulcers; immunopathological conditions requiring immunostimulation; as an organ preservation solution; and as a steroid substitute or a reducer of the effective dose of steroids.

The invention is illustrated in detail by the aid of the following non-limiting Examples.

Example 1

Preparation of
6,6'-acetylmethine-bis(2,2,4-trimethyl-1,2-dihydroquinoline) ($L_{90}$)

1300 ml of methanol, 360 g of freshly distilled 2,2,4-trimethyl-1,2-dihydroquinoline and 10 ml of concentrated hydrochloric acid were weighed in a 4-neck sulfonating bottle equipped with a stirrer, a thermometer reaching to the mixture, a portioning funnel and reflux condenser. To the reaction mixture thus obtained, 291 g of 25% aqueous methylglyoxal solution were portionwise added during 2 hours under cooling and stirring. During this period, the temperature was not allowed to exceed 30° C. After termination of the exothermic reaction, the mixture was stirred at 40° C. for 2 hours, then the pH value was adjusted between 8.0 and 8.5 by adding aqueous sodium hydroxide solution. After evaporation of methanol, the unreacted 2,2,4-trimethyl-1,2-dihydroquinoline was distilled off under a reduced pressure of 0.1 to 2 kPa at a temperature of 110 to 145° C. Then 1.5 volumes of substantially pure benzene, calculated for the volume of the residue, were added to the evaporation residue and the product was precipitated by adding heptane to the solution. Finally the product was recrystallized from isopropanol to give 270 g (67.5%) of the title compound, m.p.: 94°-96° C.

Molecular weight:
Calculated: 400;
Found by using the micromole method: 403.

Example 2

Preparation of 6,6'-acetylmethine-bis(2,2,4-trimethyl-1,2-dihydroquinoline)

1300 ml of methanol, 340 g of freshly distilled 2,2,4-trimethyl-1,2-dihydroquinoline and 20 ml of hydrochloric acid having a specific weight of 1.16 of 1.17 are weighed in a 4-neck sulfonating bottle equipped with a stirrer, a thermometer reaching to the mixture, a portioning funnel and reflux condenser. To the reaction mixture thus obtained, 146 g of acetyl methyl diacetal were portionwise added during 2 hours under cooling and stirring. During this period, the temperature was not allowed to exceed 30° C. After termination of the exothermic reaction, the mixture was stirred at 40° C. for 2 hours, then the pH value was adjusted between 10 and 12 by adding aqueous sodium hydroxide solution. After evaporation of methanol and the ethanol thus formed, the unreacted 2,2,4-trimethyl-1,2-dihydroquinoline was distilled off under a reduced pressure of 0.2 to 2kPa at a temperature of 140 to 150° C. The oily product thus obtained was distilled by 1000 g of an aqueous hydrochloride acid solution of 8% by weight, then activated charcoal was added under mixing, the reaction mixture was filtered and the pH value of the filtrate was adjusted between 10 and 11 by adding aqueous sodium hydroxide solution. The separated crystals were removed by using a nutsch filter, then dissolved in substantially pure, warm benzene, taken in a 1.5 fold amount and the product was precipitated by adding heptane to the solution. Finally the product was recrystallized from isopropanol to give 300 g (75%) of the title compound, m.p.: 101°-102° C.

Molecular weight:
Calculated: 400;

Found by using the micromole method: 401.

Example 3

Preparation of the potassium salt of 6,6'-acetylmethine-bis(2,2-dimethyl-1,2-dihydroquinoline-4-methanesulfonic acid)

400 g of 6,6'-acetylmethine-bis(2,2,4-trimethyl-1,2-dihydroquinoline) prepared as described in Example 1 was dissolved in 1200 g of 96% sulfuric acid at 60 to 85° C. The mixture obtained was maintained at the same temperature until a sample was found to be completely water-soluble. After cooling, the reaction mixture was poured into 4 to 5 liters of water under cooling and an equimolar amount of calcium hydroxide was added to the aqueous mixture. The precipitate was filtered by suction and washed with water. The filtrate was combined with the washing fluid. The compound solution contained the calcium salt of the product formed. An equimolar amount of potassium carbonate was added to this solution and the precipitated calcium carbonate was filtered by suction. After evaporating, the filtrate, the desired product was obtained which was then recrystallized from hot water to give 575 g (90%) of the title salt.

$^1$H-NMR spectrum (CDCl$_3$, δppm): —CH$_2$SO$_3$=3,94 (s, 4); =CH=5,75 (s, 2).

Molecular weight:
calculated: 638;
found: 633.

Example 4

Preparation of the sodium salt of 6,6'-acetylmethine-bis(2,2-dimethyl-1,2-dihydroquinoline-4-methanesulfonic acid)

The process described in Example 3 was followed, except that after the termination of the sulfonation the reaction mixture, cooled to room temperature, was dropwise added to 9 liters of acetone. The reaction mixture was left to stay for 24 hours, then cooled down, filtered, the recovered material washed with acetone and dried. The product thus obtained was dissolved in hot ethanol of a strength of 95%, taken in a three-fold amount, the solution filtered and the product precipitated by adding a three-fold amount of acetone. The recovered product was recrystallized again from ethanol of a strength of 95%. After cooling the white colored disulfonic acid was precipitated. From this disulfonic acid the disodium salt was prepared in an aqueous solution by adding an equimolar amount of aqueous sodium hydroxide solution. The aqueous solution was finally evaporated to dryness by using a rotating film evaporator.

Example 5

Preparation of 6,6'-ethenylmethine-bis(2,2,4-trimethyl-1,2-dihydroquinoline)

The process described in Example 1 was followed, except that 216 g of redistilled acrolein of 25% were used instead of the methylglyoxal solution.

Example 6

Preparation of 6,6'-dimethylmethine-bis(2,2,4-trimethyl-1,2-dihydroquinoline)

The process described in Example 2 was followed, except that 2 moles of 2,2,4-trimethyl-1,2-dihydroquinoline were condensed with 1 mole of acetone. The title product melted at 158°–159° C.

PREPARATION OF PHARMACEUTICAL COMPOSITIONS

Example 7

Preparation of capsules

Capsules were prepared in the usual manner by filling 200 mg of MTDQ each in soft gelatine capsules weighing 200 mg each.

Example 8

Preparation of coated tablets

Coated tablets weighing 0.5 g each were prepared as is known in the art, the components were as follows:

TABLE I

|  | mg |
| --- | --- |
| Ingredients of the core | |
| MTDQ | 250 |
| Lactose | 100 |
| Corn starch | 100 |
| Magnesium stearate | 5 |
| Polyvinylpirrolidone | 13 |
| Sodium ascorbate | 2 |
| Ingredients of the coating | |
| Pharmacoat 603 | 9.8 |
| PEG 600 | 1.5 |
| PEG 400 | 2.6 |
| Titanium dioxide | 0.2 |
| Blue pigment (Ci 73015) | 0.5 |
| Aerosil 200 | 0.4 |

Example 9

Preparation of ampoules

After weighing 1 g of the active ingredient prepared according to Example 3, each of the ampoules were deaerated by nitrogen, sealed and finally sterilized at 140° C. for 2 hours. Before use, the active ingredient was dissolved in an isotonic or infusion solution.

PHARMACOLOGICAL EXAMPLES

Example 10

Investigation of MTDO in vivo

Four women and two men (with an average age of 41 years); between 17 and 56 years participated in this study, who suffered from extrinsic bronchial asthma, and had earlier been treated with at least 20 mg/day of prednisolone (11,17,21-trihydroxypregn-4-ene-3,20-dione) or with an equivalent steroidal hormone since 2 to 15 years of age. During the experimental period, the patients were kept on the treatment commonly used for bronchial asthma, except steroidal hormones. The side effects arising from the steroidal hormone treatment could unequivocally be detected on the patients: osteoporosis was noted in all patients; steroid diabetes in two patients, steroid ulcer in two patients, Cushing-syndrome in one patient, and a severe dermal mycosis in one patient were observed.

Before admission to the intensive therapy unit, the patients were found to be in a severe asthmatic status despite the treatment mentioned above. They had a dense expiration accompanied by an enforced attack-like cough and their sputum remained tenacious.

On admission, their respiratory function characteristics were as follows:

Forced expiratory volume during 1 sec., in liter—1.00±0.16;
Tifneau value, given percentage—42%.

$$\text{Tifneau value} = \frac{\text{forced expiratory volume} \times 100}{\text{vital capacity}}$$

On the first day of experiment as a supplementation of the complex treatment, 25 mg/kg of bodyweight of MTDQ were orally administered daily in such a way that the amount of the steroidal hormone was daily decreased, the administration of the steroidal hormone was stopped on the fourth day of experiment and the complex therapy supplemented with MTDQ was continued. The clinical improvement was obvious even on the fifth day, not only the asthmatic status was solved but the patients became attack-free. Their sputum became more dilute and easy to eliminate. On auscultation, a soft vesicular respiration was again observed over their lungs. The X-ray picture of the lungs was in agreement with the clinical improvement.

On the fifteenth day of treatment, the respiratory functions were as follows:

Partial oxygen pressure in the arterial blood (age-dependent normal value)—10.9±0.45 (kPa);

Forced vital capacity (the normal value is 3.5 to 4)—3.78 ±0.33 (liter);

Forced expiratory volume (the normal value is 2.5 to 2.8)—2.06±0.8 (liter);

Partial oxygen pressure in the arterial blood—7.04±0.62 kPha;

Forced vital capacity (volume of the air taken up by a maximum inspiration expressed in liter)—1.89±0.67; Tifneau value given as percentage (the normal value is 75%) —56%.

It can be stated as an experimental result that the administration of steroidal hormone could be omitted and the status of the patients was significantly better at the end of experiment in comparison to the beginning of the experiment which was unambiguously proven to the specialist by the values of the respiratory functions.

Example 11

The experiment described in Example 10 was repeated, except that daily 300 mg of allopurinol (Milurit ®, EGIS Pharmaceutical Works) were daily administered simultaneously with the start of the MTDQ administration. As a result of this combined administration, the steroidal hormone could immediately be omitted. In the case of a prolonged treatment, the daily amount of MTDQ could be decreased from 2500 mg to 1000-1200 mg by using this combination.

Example 12

The decrease of leukotriene concentration in vitro

B. Samuelson, *Ang. Chemie*, 12, page 881 to 962 (1982) published that, in the course of various diseases, 5-hydroperoxyeicosatetraenoic acid is first formed from arachidonic acid on the effect of the lipoxygenase enzyme which then results in the formation of various leukotrienes. The mixture of leukotrienes is the so-called SRS-A mentioned above. Some leukotrienes, e.g., LTB possess a 140 to 150 times stronger effect than that of histamine, M. J. H. Smith, *J. Pharm. Pharmacol.*, 32, 411 (1980) and exert a number of harmful effects, e.g., they induce the adhesion of leukocytes, have chemotactic properties and play an important role in hypersensitivity and inflammations. In addition, they drastically increase the adhesion of leukocytes to the smallest vein capillaries. Thus, it is obvious that an active agent decreasing the concentration of leukotrienes is very useful. When such a substance diminishes the concentration of thromboxane, too (which can be determined by the measurement of $TXB_2$), a very useful active agent is obtained.

The transformation of arachidonic acid to thromboxane $B_2$ and leukotriene $B_4$ in a human leukocyte homogenate was measured by means of the method published by Tetason, J. E. et al., Brit. J. Pharmacol., 1988 94:528–529, as follows: Fresh blood, from donors who had not ingested aspirin or other drugs for at least 14 days previously, was collected, with EDTA (1.2 $mgml^{-1}$) as anticoagulant; erythrocytes were sedimented by addition of 2% methyl cellulose (7.5 ml $100^{-1}$ blood) and incubation for 40 minutes at 37° C. The supernatant containing leukocytes and platelets was removed, diluted two fold with sodium phosphate-buffered saline (0.9% NaCl, pH 7.2, 20 mM phosphate) and centrifuged for 10 minutes at 150 g. The supernatant, containing platelets, was removed and the leukocyte pellet resuspended in 50 ml of ice-cold 0.82% $NH_4Cl$ containing 5 mM KCl (brought to pH 7.4 with 4.4% $NaHCO_3$). This procedure lysed any remaining erythrocytes during 10 minutes incubation on ice. The leukocyte suspension was then centrifuged again (10 minutes, 150 g) and the pellet resuspended in 25 ml sodium phosphate buffer (50 mM, pH 7.0) containing EDTA (1 mM). The cell density was determined with a Coulter counter; differential counts made on some samples showed that the preparation contained mainly leukocytes, of which >80% were polymorphonuclear. Platelet counts were not made and no attempt was made to decrease further the platelet content of this cell suspension. The leukocyte-rich cell suspension was then centrifuged once more (10 minutes, 150 g) and the pellet was resuspended in sodium phosphate buffer (50 mM, pH 7.0) containing EDTA (1 mM) at a density of $10-20\times10^6$ cells $ml^{-1}$. Cells were homogenized by sonication. Reactions were carried out with the complete homogenate but, when appropriate, the cytoplasmic fraction was separated by centrifugation at 100,000 g for 60 minutes. Portions (0.47 ml) of homogenates were then warmed to 37° C. and 10/µl of $L_{90}$ suspension of DMSO was added.

This means DMSO sample in Table II $L_{90}$ was dissolved in DMSO to obtained concentration of 20/µMol and 100/µMol respectively. Results are shown in Table II.

DMSO was added. After further incubation (5 minutes) at 37° C. the reactions were started by addition of arachidonic acid and $CaCl_2$ (10/µl of each; final concentrations 5/µM and 2 mM, respectively). Reactions were terminated after 5 minutes at 37° C. by boiling (5 minutes). Reaction products, $TXB_2$ and $LTB_4$, were measured by specific radioimmunoassay (RIA) as published by Salmon, J. A. Prostaglandins, 1978 15: 383-397; and Salmon, J. A. et al., Prostaglandins, 1982, 24:225-235.

Blanks (boiled homogenate) and vehicle controls were included in each experiment and each reaction was carried out in triplicate.

TABLE II

The effect of $L_{90}$ (6,6'-acetylmethine-bis(2,2,4-trimethyl-1,2-dihydroquinoline) a lipid soluble radical scavenger on $LTB_4$ and $TXB_2$ formation in human leukocyte homogenate.

| Treatments (mg/ml) | $LTB_4$ (mg/ml) | $TXB_2$ |
|---|---|---|
| Untreated control 0.02 | 0.40 ± 0.36 | 0.19 ± 0.02 |
| Treated with dimethyl sulfoxide | 47.85 ± 9.98 | 1.95 ± 0.31 |
| +20/µM of the compound of Example I | 7.85 ± 2.1 | 0.68 ± 0.14 |
| +100/µM of the compound of Example I | 2.60 ± 0.37 | 0.53 ± 0.08 |

It is obvious from the data of the Table II that the concentration of $TXB_2$ was significantly decreased whereas the concentration of $LTB_4$ was highly significantly diminished. These were shown also by the analysis of the data by using Student's t-trial; namely, $p<0.005$ for $LTB_4$ and $p<0.05$ for $TXB_2$ were found.

Example 13

Tumor-inhibiting effect on the Erlich ascites tumor

A daily oral dose of 150 mg/kg of body-weight of the compound prepared in Example 1 was administered to LATI-inbred CFLP male mice weighing 20 to 22 g each for 5 days, then $2\times10^6$ of Erlich ascites tumour cells were implanted under sterile conditions. Thereafter, the drug-treatment was continued and an examination was carried out on the 16th day following the implantation. An 80% inhibition was observed on the 17th day. The percentage of inhabatation was determined as described by Zs. Pollak in the dissertation entitled "Development of a Radiosensitizing Antioxidant and Use Thereof in the Oncological Practice" pages 44 to 45 and 76 to 82, as cited above.

TABLE III

The influence of 6,6'-acetylmethine-bis(2,2,4-trimethyl-1,2-dihydroquinoline) $L_{90}$ in Ehrlich ascites tumor in mice.

|  | n | Ascites ml. | number of cells |
|---|---|---|---|
| Treated control | 20 | 15.06 + 2.85 | 96.5 × $10^7$/ml |
| $L_{90}$ 150 mg/kg | 10 | 3.95 + 0.62 | 73.3 × $10^6$/ml |

Example 14

Protection of the gastric mucosa

The protection of the gastric mucosa against the effect of ethanol was investigated. Ten CFY male rats weighing 200 to 220 g each were starved for 18 hours while allowing them to consume water ad libitum. Then, a dose of 50 or 100 mg/kg of body weight of the compound prepared in Example 1 was administered in such a way that the active agent had previously homogenized in an 1% aqueous methylcellulose solution for 1 minute. The substance was administered through a gastric tube. After 30 minutes, 1 ml of anhydrous ethanol each was orally given to the animals. Five minutes later the animals were decapitated under a general anaesthesia, their stomachs were removed, opened along the large curvature and washed with water. Thereafter the stomachs were stretched out and photographed. The alterations found on the gastric mucosa were observed by planimetry. The lesions were given as percentage of the whole surface.

Control 0%;

treated only with anhydrous ethanol 21±0.31%;

treated with anhydrous ethanol +50 mg/kg of body weight of the compound of Example 1 1.5 i 0.2%; and treated with anhydrous ethanol +100 mg/kg of body weight of the compound of Example 1 4.2±0.51%.

Based on the Student's t-trial $p<0.01$ is valid for a dose of 50 mg/kg of body-weight whereas $p<0.05$ is valid for a dose of 100 mg/kg of body weight.

Example 15

Hyperoxia-inhibiting effect

CFY rats with an average body weight of 250 g each, belonging to both sexes were kept in an atmosphere of 95% oxygen and 5% $CO_2$. Three treatment groups were formed.

Group 1 (n=100 was kept in the above mentioned oxygen and $CO_2$ atmosphere for 48 hours. 50% of the animals died within 3 days ($LD_{50}$). Autopsy and histological examinations of the animals died revealed severe and extended focal talectesia in the lungs, in addition to intra- and interalveolar oedema, hydrothorax, formation of hyalin membrane and significant amount of granular substance. The animals which survived were sacrificed in general anaesthesia on the 35th day of the experiment. Autopsy and histological examinations revealed focal dilatetion of the pulmonal interstitium, significant amount of alveolar macrophags and granular substance.

Group 2 (n=25): Hyperoxia was induced as described for Group 1, however, 20 mg/kg body weight/day i.v. Dexamethasone (steroid hormone preparation) was administered during the hyperoxia period. The rate of survival did not improve. Autopsy and histological examinations were performed on the animals died and on the animals sacrificed on the 35th day. It was remarkable that the number and severity of the pathological lesions were found less than in Group 1, however, granular substance and alveolar macrophags were present. Values of $PGF_{1C}$ and $TXB_2$ concentrations were significantly lower compared to the physiological parameters.

Group 3 (n=25): Hyperoxia was induced as in the Groups mentioned above, but during the period of hyperoxia 65 mg/kg body weight of the compound according to Example 4 was administered i.v. The rate of death amounted to 4% (1 animal). In the animals sacrificed on the 35th day of the experiment in general anaesthesia no pathological lesions were detected. It is of importance that histological investigations did not reveal the presence of granular substance alveolar macrophags, that is, protection against fybrosis is achieved.

Hyperoxia is analogue to asthma (c.f. I. Feher, G. Csomos, A. Vereckei: "Free Radical Reactions in Medicine", Springer Verlag, 1987, p. 158 and 167, references 38 and 203).

Example 16

Acute Toxicity Studies and Determination of $LD_{50}$ of the Compound $L_{90}$ (6,6'-acetylmethine-bis(2,2,4-trimethyl1,2 dihydroquinoline))

The Example was carried out in Wistar rats (Lati, Budapest) of both sexes weighing 150-160 g each. Doses of $L_{90}$ were measured by an analytical balance, for each animal and suspended in 2 ml of paraffine oil while mixing at 60° C. Suspension was then cooled to room temperature and administered through a gastric tube. Animals were fed with standard rat feed (Lati, Budapest) and received water ad libitum. They were kept at a room temperature of 23 to 25° C. The relative humidity of room air amounted to 50-70 percent. Three study groups of animals were formed.

Group 1 (n=8)

The animals received a single dose of $L_{90}$ amounting to 1 g/kg body weight.

Group 2 (n=8)

The animals received a single dose of $L_{90}$ amounting to 5 g/kg body weight.

Group 3 (n=16)

The animals received a single dose of 2 ml of paraffine oil (control group).

Animals were carefully observed on 10 subsequent days, after treatment. On day 11, the animals were sacrificed in general anesthesia. Autopsy of all animals was performed followed by the macroscopic examination of all organs.

Results

In the rats belonging to Group 1 and Group 3, no change of the behavior, appetite, and movements of the animals occurred during the observation period, on day 11 after treatment all rats were alive. Autopsy revealed no macroscopic changes and/or lesions in the vital organs.

Two rats belonging to Group 2 died on day 8 of the observation. Autopsy revealed signs of pneumonia in the lungs of both rats (possible pneumonia caused by aspiration). No other pathologic changes and/or lesions were found in their vital organs. Six animals belonging to Group 2 survived to day 11 after treatment and no change of the behavior, appetite and movements of these animals occurred, when compared to those of the animals belonging to Group 1 and Group 3 respectively. Autopsy revealed no pathologic changes in the vital organs.

Conclusion

Based on the results of the experiments described above, the $LD_{50}$ of the compound $L_{90}$ is more than 5 g/kg body Weight when administered orally to Wistar rats of both sexes.

Example 17

During model-experiments of atherosclerosis induced by atherogenic diet in rats, the pathologic increase of cythochrome C and P 450 enzyme activities is to be observed. This is disadvantageous because these enhanced enzyme activities induce tissular lipid peroxidation, involving all of its well known untoward consequences. As the first step of this chain reaction superoxyde - anion radical is formed from molecular oxygen. Laitar however initiate further few radical reactions. (J. Feher, G. Ceomos, et al., "Free Radical Reactions in Medicine" Springer Verleg Berlin, Heidelberg, New York etc. 1987, 27, 32, 60 p.; "Free radicals in Biology" Vol. V, Ed. by W. A. Pryor, Academic Press London, New-York 1982. 17-18, 23, 91 p.)

Unexpectedly it was found that on the effect of both the lipid soluble and the water soluble compound described in formula I the increased Cytochrome C and P450 activities in the rats normalized.

It has to be mentioned that Vitamin A, Vitamin C 80D —natural antioxidents—and the D-Pencillamino, (+) —Cyanidol/CatergenR/, 4-amino-5-imidozolcarboxidamide/AICAR/-synthetic antioxidants did not exert this effects in the same experiment.

It is of special interest that 2, 2, 4-trimethyl-1,2 -dihydroquinoline, the basic compound used for oxo-condensation during the synthesis of the compounds described herein and its water soluble derivative 2,2-dimethyl-4-methane-sulfonic acid salt-1,2-dihydroquinoline did not exert this effect either.

What is claimed:

1. A compound of the formula:

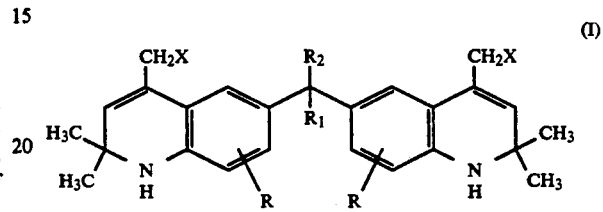

wherein:

$R_1$ is a $C_{1-6}$ alkyl group, a $(C_{1-6})$ alkylcarbonyl group, a $C_{2-6}$ alkenyl group, a hydroxy group, a $C_{1-6}$ alkoxy group, a $C_{2-6}$ alkenyloxy group, a halo-$(C_{1-6})$ alkyl group, a halo-$(C_{2-6})$ alkenyl group, a hydroxy - $(C_{1-6})$ alkyl group, a $(C_{1-6})$ alkoxy-$(C_{1-6})$ alkyl group, a $(C_{2-6})$ -alkenyloxy-$(C_{1-6})$ alkyl group, a halo-$(C_{1-6})$ alkoxy-$(C_{1-6})$ alkyl group, a halo-$(C_{2-6})$ alkenyloxy-$(C_{1-6})$ alkyl group, a carboxy-$(C_{1-6})$ alkyl group, a $(C_{1-6})$ alkoxycarbonyl-$(C_{1-6})$ alkyl group, a $(C_{2-6})$ alkenyloxycarbonyl-$(C_{1-6})$-alkyl group, a halo-$(C_{2-6})$ alkoxycarbonyl-$(C_{1-6})$-alkyl group, a halo-$(C_{2-6})$ alkenyloxycarbonyl-$(C_{1-6})$ alkyl group, a $(C_{-2-6})$ alkenylcarbonyl group, a $(C_{2-6})$ alkanoyl-$(C_{1-6})$ alkyl group, a $C(=0)$ H—$C_{1-6}$ alkyl group, a nitro-$(C_{1-6})$ alkyl group or a nitroso-$(C_{1-6})$ alkyl group or a group of the formula —$NR_3R_4$ and in the latter $R_3$ and $R_4$ may represent, independently from each other, a hydrogen atom, a $C_{1-6}$ alkyl group, a $C_{2-6}$ alkenyl group, a halo-$C_{1-6}$ alkyl group or a halo-$C_{2-6}$ alkeynl group;

R is the hydrogen or its meaning is identical to the meaning of $R_1$;

$R_2$ is hydrogen or its meaning is identical to the meaning of $R_1$;

with the proviso that $R_2$ means an alkyl group when $R_1$ is also an alkyl group and with the further proviso that it cannot be hydroxy; and X is hydrogen or —$SO_2Me$ group, where Me is an alkaline metal or earth alkaline metal atom, with the proviso that Me cannot mean barium; and if $R_1$ is an alkyl group and $R_2$ is hydrogen, then R is other than hydrogen or methyl; as well as their pharmaceutically acceptable acid addition salts.

2. The compound of claim 1 wherein $R_1$ and $R_2$ are a $C_{1-4}$ alkyl group.

3. The compound of claim 2 wherein $R_1$ and $R_2$ are the same.

4. The compound of claim 1 wherein $R_1$ and $R_2$ are an alkylcarbonyl group containing 1 to 4 carbon atoms in the alkyl moiety.

5. The compound of claim 1 wherein $R_1$ and $R_2$ are a $C_{2-4}$ alkenyl group.

6. A compound according to claim 1 and being 6,6'-acetylmethine-bis(2,2,4-trimethyl-1,2-dihydroquinoline) or a pharmaceutically acceptable salt thereof.

7. A compound according to claim 1 and being 6,6'-acetylmethine-bis(2,2-dimethyl-1,2-dihydroquinoline-methane-sulfonic acid) or a pharmaceutically acceptable salt thereof.

8. A compound according to claim 1 and being 6,6'-ethenylmethine-bis(2,2,4-trimethyl-1,2-dihydroquinoline) or a pharmaceutically acceptable salt thereof.

9. A compound according to claim 1 and being 6,6'-dimethylmethine-bis(2,2,4-trimethyl-1,2-dihydroquinoline) or a pharmaceutically acceptable salt thereof.

10. A method of treating a pathological condition where products of the metabolism of arachidonic acid contribute to the condition comprising administering to a mammal in need of such treatment an effective amount of the compound of claim 1.

11. A method of substantially simultaneously inhibiting a cyclooxygenase pathway and a lipoxygenase pathway in a mammal suspected of requiring said inhibition comprising administering to the mammal an effective amount of the compound of claim 1.

12. A method of normalizing pathologically changed cytochrome C and P450 values comprising administering to a mammal in need of such treatment an effective amount of the compound of claim 1.

13. The method of claim 10 wherein the pathological condition is asthma.

14. A pharmaceutical composition comprising the compound of claim 1 in a pharmaceutically acceptable carrier.

15. A method of preventing gastric injuries in a mammal in need of such treatment comprising administering to said mammal an effective amount of the compound of claim 1.

16. A method of substantially simultaneously inhibiting a cyclooxygenase pathway and a lipoxygenase pathway in a mammal suspected of requiring said inhibition comprising administering to the mammal an effective amount of a compound of the formula:

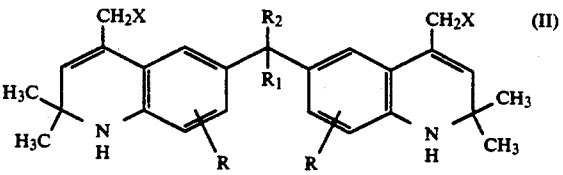

wherein:
$R_1$ is a $C_{1-6}$ alkyl group, a $(C_{1-6})$ alkylcarbonyl group, a $C_{2-6}$ alkenyl group, a hydroxy group, a $C_{1-6}$ alkoxy group, a $C_{2-6}$ alkenyloxy group, a halo-$(C_{1-6})$ alkyl group, a halo-$(C_{2-6}$ alkenyl group, a hydroxy-$(C_{1-6})$ alkyl group, a $(C_{1-6})$ alkoxy-$(C_{1-6})$alkyl group, a $(C_{2-6})$-alkenyloxy-$(C_{1-6})$ alkyl group, a halo-$(C_{1-6})$ alkoxy-$(C_{1-6})$ alkyl group, a halo-$(C_{2-6})$ alkenyloxy-$(C_{1-6})$ alkyl group, a carboxy-$(C_{1-6})$ alkyl group, a $(C_{1-6})$ alkoxycarbonyl-$(C_{1-6})$ alkyl group, a $(C_{2-6})$ alkenyloxycarbonyl-$(C_{1-6})$-alkyl group, a halo-$(C_{2-6})$ alkoxycarbonyl-$(C_{1-6})$-alkyl group, a halo-$(C_{2-6})$ alkenyloxycarbonyl-$(C_{1-6})$ alkyl group, a $(C_{-2-6})$ alkenylcarbonyl group, a $(C_{2-6})$ alkanoyl-$(C_{1-6})$ alkyl group, a $C(=O)$ H—C-1-6 alkyl group, a nitro-$(C_{1-6})$ alkyl group or a nitroso-$(C_{1-6})$ alkyl group or a group of the formula —$NR_3R_4$ and in the latter $R_3$ and $R_4$ may represent, independently from each other, a hydrogen atom, a $C_{1-6}$ alkyl group, a $C_{2-6}$ alkenyl group, a halo-$C_{1-6}$ alkyl group or a halo-$C_{2-6}$ alkeynl group;

R is hydrogen or its meaning is identical to the meaning of $R_1$, $R_2$ is hydrogen or its meaning is identical to the meaning of $R_1$, with the proviso that it cannot be hydroxy; and X is hydrogen or —$SO_2Me$ group, where Me is an alkaline metal or earth alkaline metal atom, with the proviso that Me cannot mean barium;

as well as their pharmaceutically acceptable acid addition salts.

17. A method of treating a pathological condition where products of the metabolism of arachidonic acid contribute to the condition comprising administering to a mammal in need of such treatment an effective amount of the compound of formula II as described in claim 16.

18. The method of claim 17 wherein the pathological condition is asthma.

19. A method of normalizing pathologically changed cytochrome C and P450 values comprising administering to a mammal in need of such treatment an effective amount of the compound of formula II as described in claim 16.

* * * * *